United States Patent [19]
Itoigawa et al.

[11] Patent Number: 5,836,886
[45] Date of Patent: Nov. 17, 1998

[54] CATHETER HAVING A SENSOR

[75] Inventors: Koichi Itoigawa; Hitoshi Iwata; Kenichi Kinoshita, all of Aichi-ken, Japan

[73] Assignee: Kabushiki Kaisha Tokai Rika Denki Seisakusho, Japan

[21] Appl. No.: 739,378

[22] Filed: Oct. 29, 1996

[30] Foreign Application Priority Data

Nov. 1, 1995 [JP] Japan .................................. 7-285369

[51] Int. Cl.⁶ ...................................................... A61B 5/02
[52] U.S. Cl. ........................ 600/488; 600/561; 600/587; 73/746
[58] Field of Search ..................................... 600/381, 433, 600/434, 435, 485, 486, 488, 561, 587; 73/4 R, 708, 720, 721, 725–727, 744–746

[56] References Cited

U.S. PATENT DOCUMENTS

| | | | |
|---|---|---|---|
| 3,911,902 | 10/1975 | Delpy . | |
| 3,946,724 | 3/1976 | La Balme . | |
| 4,722,348 | 2/1988 | Lightenberg et al. | 600/488 |
| 4,846,191 | 7/1989 | Brockway et al. | 600/486 |
| 5,113,868 | 5/1992 | Wise et al. | 600/488 |
| 5,209,120 | 5/1993 | Araki | 600/488 |
| 5,257,630 | 11/1993 | Broitman et al. | 600/488 |
| 5,425,371 | 6/1995 | Mischenko | 600/488 |
| 5,517,998 | 5/1996 | Madison | 600/488 |
| 5,661,245 | 8/1997 | Svoboda et al. | 73/726 |

FOREIGN PATENT DOCUMENTS 6-190050  7/1994  Japan .

*Primary Examiner*—Jennifer Bahr
*Assistant Examiner*—Bryan K. Yarnell
*Attorney, Agent, or Firm*—Quarles & Brady

[57] ABSTRACT

A catheter that is guided into an intra-corporeal passageway is set forth. A catheter tube accommodates an element having a piston for detecting a pressure in the intra-corporeal passageway. Silicone gel is accommodated in the catheter tube to transmit the detected pressure in the catheter tube. A strain gage is disposed on a semiconductor chip to output an electric signal based on an amount of a deformation thereof indicative of the pressure in the catheter tube.

6 Claims, 3 Drawing Sheets

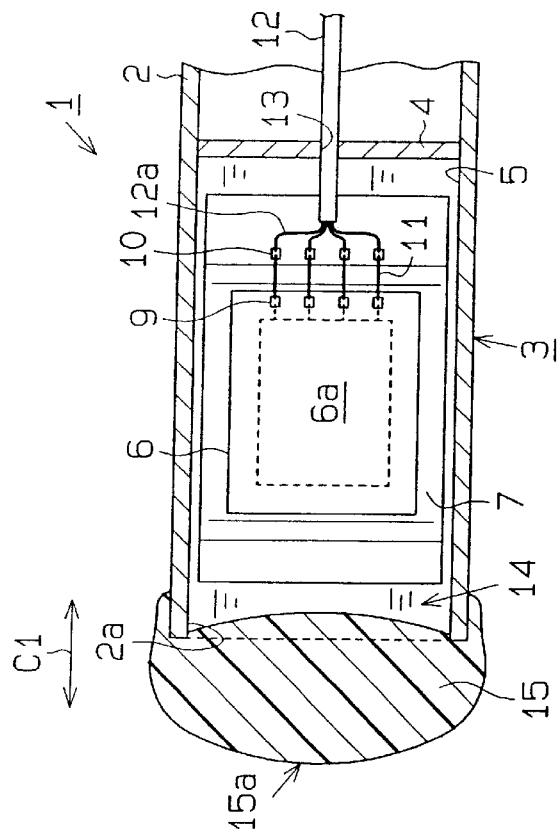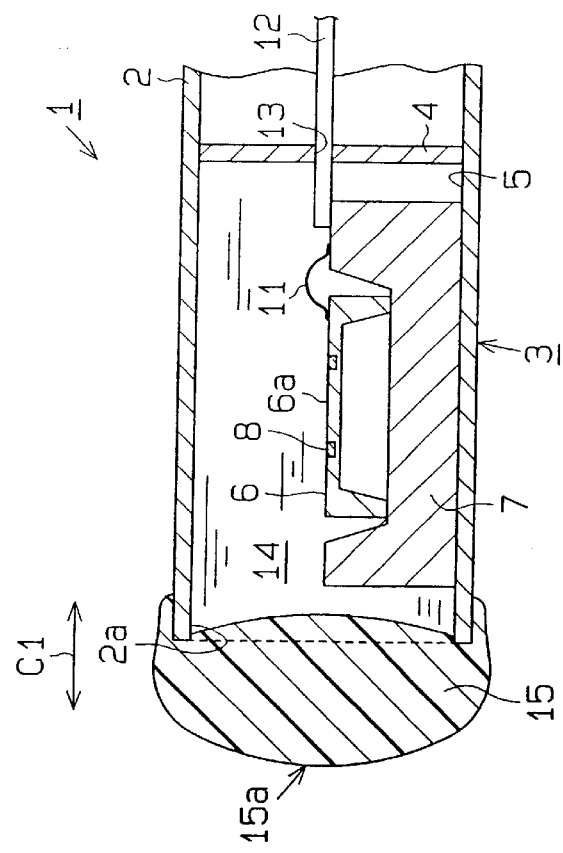

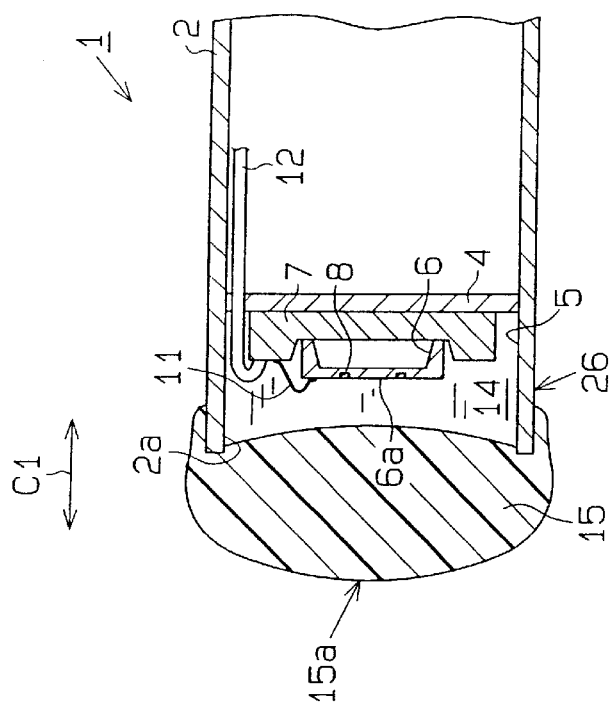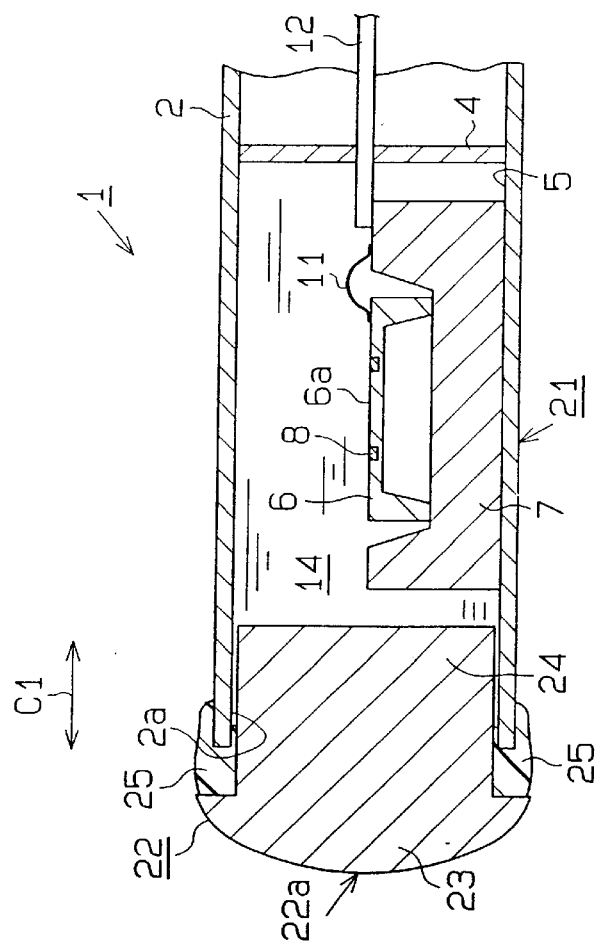

CATHETER HAVING A SENSOR

BACKGROUND OF THE INVENTION

1. Field of the Invention

The present invention relates to a catheter that has a sensor provided on its distal end. More particularly, the present invention relates to a catheter having a sensor at its distal end, which is guided into an intra-corporeal passageway.

2. Description of the Related Art

Catheters are medical devices that are inserted into the human body. A catheter has a flexible catheter tube, the diameter of which is a few millimeters. The tube is inserted in intra-corporeal passageways, such as blood vessels. The distal end of the tube is guided to a desirable point where it performs measuring (e.g., measurement of the blood pressure) or medical treatment (e.g., vasodilation). The doctor manipulates the tube from the outside of the patient's body in order to guide the distal end of the tube to the desirable point.

The intra-corporeal passageways are curved and branched and their diameters vary at different locations. In addition, obstacles such as a thrombus may narrow the passageways.

However, prior art catheters do not have means to confirm the state of the intra-corporeal passageway at their front ends. Therefore, it is required for the doctor to maneuver the catheter to the desirable position based on his or her instincts and experience.

To facilitate the maneuvering of the catheter, there is a need for a sensor be mounted on the distal end of a catheter tube to allow the state of the passageway in front of the catheter be confirmed as the catheter advances therein.

SUMMARY OF THE INVENTION

Accordingly, it is an objective of the present invention to provide a catheter that has a sensor to detect the conditions in front of the catheter.

It is another objective of the present invention to provide a compact sensor.

To achieve the above objectives, a catheter that is guided into an intra-corporeal passageway is disclosed. The catheter includes a sensor located at an end of the catheter tube to sense pressure in the intra-corporeal passageway and to transmit the detected pressure into the catheter tube, a pressure medium accommodated in the catheter tube to control the pressure in the catheter tube based on the pressure transmitted from the sensor and a device in the catheter tube for issuing an electric signal indicative of changes in the pressure controlled by the pressure medium.

BRIEF DESCRIPTION OF THE DRAWINGS

The features of the present invention that are believed to be novel are set forth with particularity on the appended claims. The invention, together with objects and advantages thereof, may best be understood by reference to the following description of the presently preferred embodiment together with the accompanying drawings in which:

FIG. 1 is a schematic cross-sectional side view illustrating the distal end of a catheter according to a first embodiment of the present invention;

FIG. 2 is a schematic cross-sectional top view illustrating the distal end of the catheter of FIG. 1;

FIG. 3 is a schematic cross-sectional side view illustrating the distal end of a catheter according to a second embodiment of the present invention;

FIG. 4 is a schematic cross-sectional side view illustrating the distal end of a catheter according to a third embodiment.

DETAILED DESCRIPTION OF THE PREFERRED EMBODIMENTS

Figure 5:
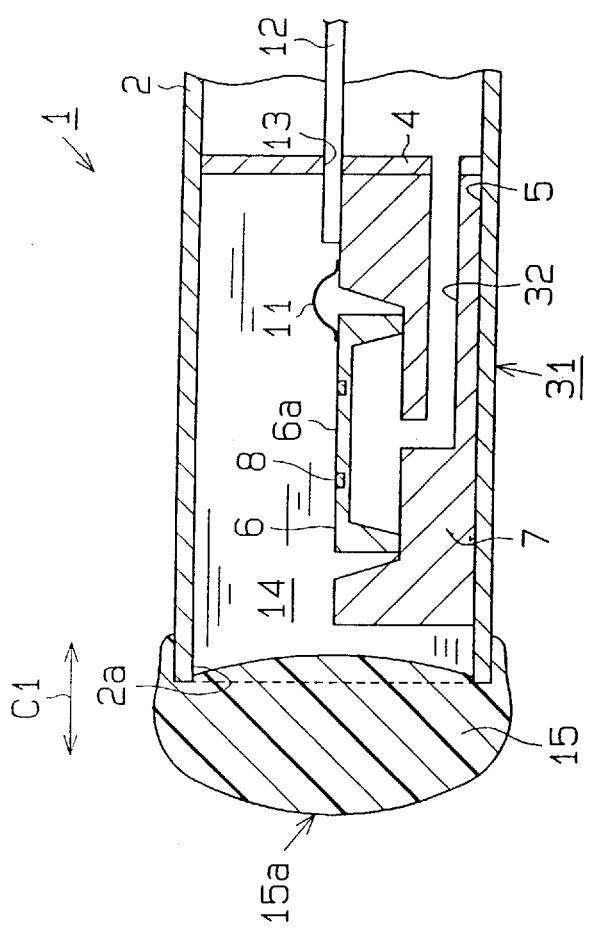
FIG. 5 is a schematic cross-sectional side view illustrating the distal end of a catheter according to a fourth embodiment.

A blood vessel catheter according to a first embodiment of the present invention will be described below with reference to FIGS. 1 and 2.

A blood vessel catheter 1 has a catheter tube 2 and a manipulator (not shown) attached to the proximal end of the tube 2 for manipulating the tube 2 from the outside of the body. The manipulator includes a plurality of wires provided in the tube 2 and a device for moving the wires.

The catheter 1 has a sensor 3 as described below provided at the distal end of the tube 2. A partition plate 4 is provided in the tube 2. The partition plate 4 defines a sensor chamber 5 at the distal end of the tube 2. A rectangular substrate 7 is accommodated in the chamber 5. A rectangular chip 6 is mounted on the substrate 7. The chip 6 and the substrate 7 are arranged with their longer sides parallel to the longitudinal axis of the tube 2 (or parallel to the line C1) and their shorter sides perpendicular to the axis of the tube 2 (or perpendicular to the line C1). The shorter sides of the substrate 7 are slightly shorter than the inner diameter of the tube 2, while its longer sides are slightly longer than the inner diameter of the tube 2.

Using the extremely small chip 6 minimizes the size of the sensor 3. The plane of the pressure sensing surface 6a of the chip 6 is arranged parallel to the longitudinal axis of the tube 2. This enables the diameter of the sensor 3 to be smaller than when the surface 6a is arranged perpendicular to the axis of the tube 2. Accordingly the diameter of the catheter tube 2 is minimized.

A thin section is provided at the top of the chip 6. The thin section has a pressure sensing surface 6a on its top. Strain gauges 8 are provided on the pressure sensing surface 6a. A plurality of pads 9, 10 are arranged on the chip 6 and the substrate 7, respectively. Each pad 9 is connected to one of the pads 10 by a bonding wire 11. One of lead wires 12a in a signal cable 12 is connected to one of the pads 10 on the substrate 7. The cable 12 extends through the tube 2 from its proximal end to its distal end of the tube 2. The distal end of the cable 12 extends through the hole 13 of the plate 4.

The chamber 5 is filled with silicon gel 14. The opening 2a of the tube 2 is sealed with a seal 15. The exposed side of the seal 15 serves as a pressure receiving surface 15a. The seal 15 is made of biocompatible resin, such as polytetrafluoroethylene (PTFE) or chloroethylene.

The operation of the above catheter 1 will now be described.

Changes in conditions inside a blood vessel may increase the insertion resistance of the catheter tube 2. This alters the pressure applied to the pressure receiving surface 15a of the tube 2. For example, the insertion resistance of the catheter tube 2 increases when the catheter 1 is pressed against an obstacle (a thrombus or a tumor) or a narrowed part in a vessel. Accordingly, the pressure applied to the surface 15a of the seal 15 increases. This increases the pressure of the gel 14 in the chamber 5, thereby increasing the pressure applied on the pressure sensing surface 6a.

More specifically, changes in the external pressure applied to the sensor 3 is transmitted to the pressure sensing surface 6a by the gel 14. This strains the pressure sensing surface 6a and changes the resistance value of the strain gauge 8. The chip 6 converts the pressure changes into electrical signals and transmits the signals to the electrical circuit at the proximal end of the tube 2 via the bonding wires 11 and the cable 12. The circuit processes and visualizes the signals. The visualized data allows the doctor to judge the conditions in the vessel, e.g., existence of obstacles or narrowed passages in the vessel.

The doctor adjusts the advancing direction of the tube 2 by manipulating the wires until the visualized data shows a decrease in the insertion resistance of the tube 2. This allows the doctor to further advance the catheter tube avoiding obstacles or narrow passages to the predetermined point.

The sensor 3 may also be used for other purposes, for example, measuring blood pressure.

The partition plate 4, which parts the interior of the tube 2, prevents the pressure acting on the gel 14 from escaping toward the proximal direction. This minimizes the difference in the increased pressure acting on the pressure receiving surface 15a and the increased pressure acting on the gel 14. Accordingly, the pressure acting on the surface 15a is accurately transmitted to the pressure sensing surface 6a. This improves the sensitivity of the sensor 3. The partition plate 4 also enables the gel to be easily filled into the sensor chamber 5 from the distal end of the tube 2.

In this embodiment the silicon gel 14 is used as pressure transmitting medium. Accordingly, changes in the pressure applied to the pressure receiving surface 15a are accurately transmitted to the pressure sensing surface 6a even when the surfaces 15a, 6a are arranged in different directions. This improves the sensitivity of the sensor 3 compared to a sensor using a non-fluid material as the pressure transmitting medium. The seal 15 and the partition 4 also ensures the sealing of the gel 14 in the chamber 5.

In this embodiment the seal 15 is made of a biocompatible material. Therefore when contacting organic material, such as blood, the sensor 3 does not form a thrombus in the vessel. This means that the catheter 1 has a high compatibility with organisms. Using silicon gel 14, which is also a biocompatible material, further improves the catheter's compatibility with organisms.

A second embodiment according to the present invention will now be described with reference to FIG. 3.

A sensor 21 of a catheter 1 may employ a piston 22 instead of the seal 15. The piston 22 consists of a piston body 24 and a flange 23. The piston body 24 is slidably inserted in the tube 2. The space between the opening 2a of the tube 2 and the flange 23 is sealed with silicon rubber 25. The outer surface of the flange 23 serves as a pressure receiving surface 22a. The piston 22 slides in accordance with pressure applied to the surface 22a. Accordingly, the pressure is transmitted to the silicon gel 14.

The piston 22 of this embodiment is made of biocompatible material.

A third embodiment according to the present invention will now be described with reference to FIG. 4.

The pressure sensing surface 6a of the chip 6 in a sensor 26 is arranged parallel to the pressure receiving surface 15a, that is, perpendicular to the longitudinal axis of the tube 2 (or perpendicular to the line C1). The sensor 26, though having a larger diameter than the sensor 3, positively transmits the pressure acting on the surface 15a to the pressure sensing surface 6a.

A fourth embodiment according to the present invention will now be described with reference to FIG. 5.

A relative pressure type sensor 31 may be used in the catheter 1. The sensor 31 has a pressure releasing hole 32 formed in the substrate 7. The hole 32 communicates the space between the chip 6 and the substrate 7 with the interior of the tube 2.

Therefore, the present examples and embodiments are to be considered as illustrative and not restrictive and the invention is no to be limited to the details given herein, but may be modified within the scope of the appended claims. The modifications are as follows:

(A) The substrate 7 may be employed as the partition plate 4. Further, the substrate 7 may be omitted by mounting the chip 6 directly on the inner wall of the catheter tube 2.

(B) Instead of the sensors 3, 21, 26 formed integrally with the tube 2, a sensor formed separately from the tube 2 may be used.

(C) Instead of silicon gel 14, other gel materials may be used as the pressure transmitting medium. Further a fluid material, such as silicon oil, may be used as the pressure transmitting material. However, taking the so-called "dance" phenomenon of the medium into account, utilizing gel material such as the silicon gel 14 is more preferable.

What is claimed is:

1. A catheter that is guided into an intra-corporeal passageway, said catheter comprising:

a catheter tube having a longitudinal axis;

means located at an end of the catheter tube to detect pressure in the intra-corporeal passageway, said detecting means including a piston member slidably attached to a distal end of the catheter tube, said piston member being arranged to project and retract with respect to the end of the catheter tube based on the pressure in the intra-corporeal passageway;

a pressure media accommodated in the catheter tube to transmit the detected pressure in the catheter tube, said pressure media consisting of either a gel or a liquid; and means for outputting an electric signal indicative of the pressure in the catheter tube, said outputting means being disposed in the catheter tube and including a rectangular substrate, a rectangular semiconductor chip disposed on the substrate, and a strain gauge provided within the semiconductor, said substrate and semiconductor chip having a longitudinal axis extending in the same direction as the longitudinal axis of said catheter tube.

2. The catheter as set forth in claim 1, wherein said piston member is made of biocompatible resin.

3. The catheter as set forth in claim 1, wherein the pressure media includes biocompatible silicone gel.

4. A catheter that is guided into an intra-corporeal passageway, said catheter comprising:

a catheter tube having a longitudinal axis;

means located at a tip of the catheter tube to detect pressure in the intra-corporeal passageway, said detecting means including a piston member slidably attached to a distal end of the catheter tube, said piston member being arranged to project and retract with respect to the distal end of the catheter tube based on the pressure in the intra-corporeal passageway;

silicone gel accommodated in the catheter tube to transmit the detected pressure in the catheter tube; and a rectangular semiconductor chip supported on a rectangular substrate and located in the catheter tube, said substrate and semiconductor chip having a longitudinal axis extending in the same direction as the longitudinal axis of said catheter tube, said semiconductor chip supporting a strain gauge outputting an electric signal based on an amount of a deformation thereof, which is indicative of the pressure in the catheter tube.

5. The catheter as set forth in claim 4, wherein said piston member is made of biocompatible resin.

6. The catheter as set forth in claim 4, wherein said pressure media includes biocompatible silicone gel.

* * * * *